United States Patent [19]
Oku et al.

[11] Patent Number: 5,882,808
[45] Date of Patent: Mar. 16, 1999

[54] ANTI-BACTERIAL AND ANTI-FUNGAL CERAMIC PRODUCT

[75] Inventors: Takashi Oku; Keijiro Shigeru; Takako Yazawa; Tomohiko Iijima; Nobuyuki Kumakura, all of Funabashi, Japan

[73] Assignee: Sumitomo Osaka Cement Co., Ltd., Tokyo, Japan

[21] Appl. No.: 523,880

[22] Filed: Sep. 6, 1995

Related U.S. Application Data

[63] Continuation of Ser. No. 379,487, filed as PCT/JP94/00873, May 31, 1994, abandoned.

[30] Foreign Application Priority Data

May 31, 1993 [JP] Japan .................................. 5-129418
Oct. 5, 1993 [JP] Japan .................................. 5-249590
Apr. 18, 1994 [JP] Japan .................................. 6-79064

[51] Int. Cl.⁶ ...................................................... B32B 9/00
[52] U.S. Cl. ........................... 428/699; 428/701; 428/702
[58] Field of Search ............................... 501/19; 428/688, 428/699, 701, 702; 4/538, 619, 222

[56] References Cited

U.S. PATENT DOCUMENTS 3,441,516  4/1969  Mulligan .................................. 501/19

FOREIGN PATENT DOCUMENTS 5-201 747  8/1993  Japan .
6-127 975  5/1994  Japan .

Primary Examiner—Timothy M. Speer
Attorney, Agent, or Firm—Kane, Dalsimer, Sullivan, Kurucz, Levy, Eisele and Richard

[57] ABSTRACT

The present invention provides an anti-bacterial and anti-fungal glaze composition for ceramic products formed by incorporating a silver-containing substance; and a fire resistant material and/or glass composition. The present invention can be used in the manufacture of ceramic products requiring sanitary properties such as tile, sanitary earthenware, commodes, bath tubs and the like, and according to the present invention, anti-bacterial and anti-fungal properties can be effectively exhibited therein. In particular, the present invention can be used in sink basins, tile, commodes, bath tubs, and the like of hospitals, hotels and public facilities.

15 Claims, 1 Drawing Sheet

ANTI-BACTERIAL AND ANTI-FUNGAL CERAMIC PRODUCT

This is a continuation of application Ser. No. 08/379,487, filed as PCT/JP94/00873, May 31, 1994 now abandoned.

FIELD OF THE TECHNOLOGY

The present invention relates to an anti-bacterial and anti-fungal glaze composition for ceramic products. More concretely, the present invention relates to an anti-bacterial and anti-fungal glaze composition for ceramic products incorporating a silver-containing substance which is useful in imparting anti-bacterial and anti-fungal properties to ceramic products such as porcelain, enamel products and the like.

BACKGROUND ART

Products such as commodes, wash bowels and bath tubs, due to frequent direct contact with the skin of humans or frequent close encounters with the skin, require sanitary properties, as well as an appealing external appearance. In order to satisfy these aforementioned requirements, products such as the aforementioned commode are made from ceramic products.

The reason for the aforementioned is because the surface of the ceramic products is glaze, i.e., coated using glass, and this glaze layer which is a fine layer of a glass substance formed from glaze does not absorb water and, in addition, possesses a smooth surface which is difficult to damage. Therefore, these ceramic products have sufficiently satisfied the demands regarding sanitation and an appealing external appearance.

However, recently, the requirements, from a sanitary perspective, have further increased with respect to tile and sanitary earthenware, in addition to the aforementioned products. In particular, in hospitals in which MRSA (methicillin-resistant *Staphylococcus aureus*) is causing problems, the requirements from a sanitary perspective have further increased with respect to ceramic products such as the tile used for floors, walls of operating rooms, and the like, as well as commodes.

However, the conventional glaze does not inherently possess anti-bacterial and anti-fungal properties and consequently, does not possess the ability to kill bacterium and fungi adhering to the surfaces of the aforementioned ceramic products.

DISCLOSURE OF THE INVENTION

The present invention provides an anti-bacterial and anti-fungal glaze composition for ceramic products incorporating a silver-containing substance; a fire resistant material formed from clay, agalmatolite, diaspore, bauxite, alumina silicate and the like; and/or an oxide glass composition such as soda-lime glass, lead glass, borosilicate glass, alumino-silicate glass and the like. Hence, anti-bacterial and anti-fungal effects can be generated by means of the silver component in the aforementioned silver-containing substance such that it is possible to form an anti-bacterial and anti-fungal glaze layer and enamel surface possessing superior anti-bacterial and anti-fungal properties on the surfaces of ceramic products employing the aforementioned.

This anti-bacterial and anti-fungal glaze composition for ceramic products possesses an improved heat resistance due to the aforementioned fire resistant material and/or glass composition, and can exhibit superior anti-bacterial and anti-fungal properties even when applied to ceramic products produced by baking at high temperatures.

In addition, in the present invention, the anti-bacterial and anti-fungal glaze composition for ceramic products is specified as a material for coating onto a previously formed glaze layer and then baking to form an anti-bacterial and anti-fungal glaze layer possessing anti-bacterial and anti-fungal properties. However, depending on the situation, this anti-bacterial and anti-fungal glaze composition for ceramic products may also be used to form an anti-bacterial and anti-fungal glaze layer by mixing with a conventional glaze which does not possess anti-bacterial and anti-fungal properties; coating onto a substrate prior to baking or coating onto a baked substrate which has been baked once; and then baking. Additionally, the aforementioned composition may be used to form an anti-bacterial and anti-fungal glaze layer by means of coating onto the substrate of a ceramic product or a baked substrate itself followed by baking.

PREFERRED EMBODIMENTS OF THE INVENTION

Figure 1:
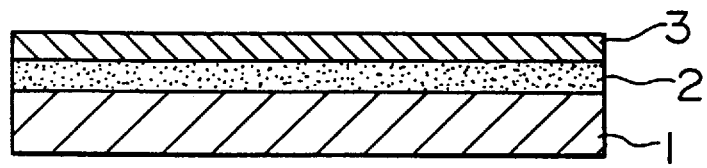
FIG. 1 is a structural outline showing an embodiment in which an anti-bacterial and anti-fungal glaze composition for ceramic products according to the present invention is applied to a glaze layer previously formed on the substrate of a ceramic product.

The inventors of the present invention have researched various means for imparting anti-bacterial and anti-fungal properties to ceramic products and have completed the present invention by solving the aforementioned problems through the use of a silver-containing substance and improvement of the heat resistance therein.

In the past, it was clear that some metals such as silver exhibited anti-bacterial properties; however, up until now the use of substances incorporating these metals, in order to impart this property to the glaze layer and enamel surface of ceramic products, has been difficult.

In other words, in the case where these metals and metal-incorporating substances were coated on the conventional glaze lacking anti-bacterial and anti-fungal properties, or in the case where these metals and metal-incorporating substances were mixed with the conventional glaze and the mixture was coated, after baking, discoloration as well as degradation of the surface shape of the glaze layer and enamel surface were observed with regard to ceramic products possessing various color and surface shapes.

Furthermore, since in general, substances incorporating metals such as silver melt at a lower temperature than the baking temperature of ceramic products, the metal component exhibiting anti-bacterial and anti-fungal properties often sinks into the interior and/or bottom portions of the glaze, which in turn leads to a predominant or total loss of this metal component from the surface of the ceramic product actually in contact with the bacterium and fungi, i.e., the enamel surface. Thus, until recently, it was not possible to exhibit the desired anti-bacterial and anti-fungal effects.

In other words, the anti-bacterial and anti-fungal glaze composition for ceramic products according to the present invention imparts anti-bacterial and anti-fungal properties to aforementioned glaze layer and enamel surface by means of being incorporated into the glaze layer and enamel surface formed on the surfaces of the ceramic products. Therefore, the present invention is characterized in that a silver-containing substance and a fire resistance material and/or glass composition is incorporated into the aforementioned composition.

The silver-containing substance for use in the present invention, although not particularly limited, is preferably selected from among metallic silvers, halogenated silvers (e.g., fluorinated silver, chlorinated silver and the like), silver salts of inorganic acids (e.g., water soluble inorganic silver salts such as silver nitrate, as well as inorganic salts which are slightly soluble in water such as silver carbonate, silver phosphate and the like), silver salts of organic acids (e.g., silver citrate), silver oxides and silver hydroxides.

In addition, without being limited to the aforementioned, the silver-containing substance to be used in the present invention can also be selected from among ion-exchange compounds which carry silver as a result of an ion-exchange reaction. This type of ion-exchange compound is preferably an inorganic compound, and can be appropriately selected from aluminum silicate compounds, phosphate compounds (e.g., calcium phosphate, zirconium phosphate, and the like), titania compounds (e.g., titania), silica compounds (e.g., silica gel) and the like.

In addition, as the fire resistant material to be used in the present invention there can be mentioned clay, agalmatolite, diaspore, bauxite, alumina silicate and the like; however, the fire resistant material is not limited to the aforementioned, and these fire resistant materials may be used alone or multiple combinations.

The types of glass compositions to be used in the present invention are not limited to any particular composition, and can be appropriately selected from among the aforementioned oxide glasses or glass compositions used as glaze in porcelain and enamel according to the conventional art.

The incorporation amount of the silver-containing substance in the anti-bacterial and anti-fungal glaze composition for ceramic products according to the present invention is preferably 0.01~40% by weight when converted to metallic silver. When the incorporation amount of the silver-containing substance is less than 0.01% by weight, the anti-bacterial and anti-fungal properties of the resultant glaze layer and enamel surface are insufficient for practical use. On the other hand, when the aforementioned incorporation amount exceeds 40% by weight, undesirable changes occur with respect to the color and material of the resultant glaze layer and enamel surface. In general, as long as the incorporation amount of the silver-containing substance is within the range of 0.01~40% by weight, extreme detrimental effects are not imparted to the manageability and coat properties of the anti-bacterial and anti-fungal glaze composition for ceramic products, as well as to the color and material of the glaze layer and enamel surface.

In the following, an example of the anti-bacterial and anti-fungal ceramic product employing the anti-bacterial and anti-fungal glaze composition for ceramic products of the present invention will be explained.

This anti-bacterial and anti-fungal ceramic product employing the anti-bacterial and anti-fungal glaze composition for ceramic products is formed by applying the anti-bacterial and anti-fungal glaze composition for ceramic products according to the present invention on the substrate of a ceramic product such as earthenware, porcelain or the like, followed by baking and fixing therein. This example is shown in FIGS. 1~3.

Figure 2:
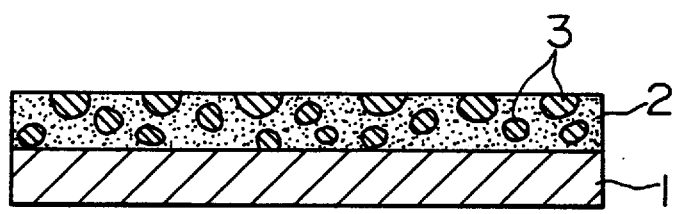
FIG. 2 is a structural outline showing an embodiment in which an anti-bacterial and anti-fungal glaze composition for ceramic products according to the present invention is mixed and used with a conventional glaze which does not possess anti-bacterial and anti-fungal properties.
Figure 3:
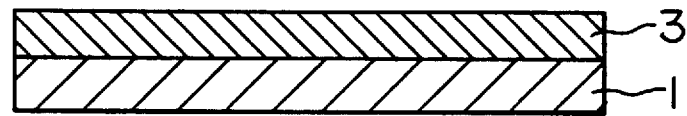
FIG. 3 is a structural outline showing an embodiment in which an anti-bacterial and anti-fungal glaze composition for ceramic products according to the present invention is applied directly to the substrate of a ceramic product.

As shown in FIGS. 1~3, a substrate 1 of a ceramic product; glaze layer 2 formed from conventional glaze which does not possess anti-bacterial and anti-fungal properties; and anti-bacterial and anti-fungal glaze layer 3 formed from an anti-bacterial and anti-fungal glaze composition for ceramic products are provided. In these figures, the anti-bacterial and anti-fungal glaze composition for ceramic products is either laminated, dispersed, or directly affixed to the substrate of the ceramic product via a conventional glaze lacking anti-bacterial and anti-fungal properties.

As the process for affixing the aforementioned, any conventional process can be used, for example, the material shown in FIG. 1 is formed by means of coating and drying a conventional glaze, and then spraying and baking a dispersion fluid, in which the aforementioned anti-bacterial and anti-fungal glaze composition for ceramic products is dispersed in an appropriate solvent such as water or the like, onto the surface of a ceramic product to be imparted with anti-bacterial and anti-fungal properties.

In addition, the material shown in FIG. 2 is formed by means of dispersing and mixing an anti-bacterial and anti-fungal glaze composition for ceramic products with a conventional glaze, applying this mixture to a substrate, and then baking. In this manner, it is possible to simplify the aforementioned process.

Furthermore, the material shown in FIG. 3 is formed by means of spraying the anti-bacterial and anti-fungal glaze composition for ceramic products directly onto a substrate, and then baking. In this composition, it is possible to impart anti-bacterial and anti-fungal properties to the non-glazed sections by selecting a silver-containing substance and fire resistant material.

Therefore, by means of the aforementioned processes, it is possible to form a glaze layer and enamel surface possessing anti-bacterial and anti-fungal properties on the surface of a ceramic product. However, the present invention is not limited to the aforementioned processes. Furthermore, the number of applications of the glaze can also be appropriately designated.

In addition, the coating method at this time can be optionally selected from among spray, dash and dip coating methods. Similarly, the conditions at the time of baking, e.g., baking temperature and the like, can be optionally designated depending on the use and the like of the ceramic product to be produced.

This type of anti-bacterial and anti-fungal ceramic product is produced by forming an anti-bacterial and anti-fungal glaze layer from the anti-bacterial and anti-fungal glaze composition for ceramic products according to the present invention. In this manner, the silver-containing substance possessing anti-bacterial and anti-fungal properties is dispersed in the aforementioned glaze layer and enamel surface, thus anti-bacterial and anti-fungal properties can be exhibited with a high efficiency since the aforementioned silver component reliably exists in the aforementioned enamel surface.

In addition, it is possible to form an anti-bacterial and anti-fungal ceramic product without any special processes by means of employing a conventional method for manufacturing porcelain and/or earthenware in which the anti-bacterial and anti-fungal glaze composition for ceramic products according to the present invention is coated onto a surface therein and then baked. Thus in the manufacture of ceramic products, it is not necessary to make any drastic procedural modifications.

In the following, the evaluation method of the validity of the anti-bacterial and anti-fungal glaze composition for ceramic products according to the present invention, as well as the results therein will be explained.

EXAMPLES 1~12 AND COMPARATIVE EXAMPLE 1

In each of Examples 1~12 and Comparative Example 1, a glaze of the following composition was employed:

| | |
|---|---|
| $SiO_2$ | 55 parts by weight |
| $ZrO_2$ | 10 parts by weight |
| $Al_2O_3$ | 10 parts by weight |
| CaO | 10 parts by weight |
| ZnO | 10 parts by weight |
| $K_2O$ | 4 parts by weight |
| $Na_2O$ | 1 part by weight |

The silver-containing substance shown in Table 1 was mixed into this aforementioned glaze at a ratio of 0.1% by weight when converted to the weight of metallic silver, and the resultant mixture was dispersed in water to form a dispersion fluid of an anti-bacterial and anti-fungal glaze composition for ceramic products as a white emulsion. This dispersion fluid was coated onto tile to which a conventional glaze had been previously applied at a coating amount of 30 g/m$^2$ (solid content weight), dried and then baked for 1 hour at a temperature of 1200° C.

In order to test the anti-bacterial and anti-fungal properties of the resultant products, a halo test and fungus resistance test were performed.

The aforementioned halo test consisted of placing the test specimen on a normal agar culture medium onto which bacterium in a liquid suspension had been coated, allowing this test specimen to sit in an incubator for 18 hours at 37° C., and then measuring the width of the inhibition band formed around the periphery of the test specimen.

The fungus resistance test consisted of placing the test specimen on an agar of potato dextrose, sprinkling a liquid spore suspension from above this test specimen, and then observing for the generation of fungus on the test specimen with the naked eye.

The results of the halo tests are shown in Table 2.

TABLE 1

| | |
|---|---|
| Example 1 | $AgNO_3$ |
| Example 2 | $AgCO_3$ |
| Example 3 | AgCl |
| Example 4 | Ag |
| Example 5 | Silver citrate |
| Example 6 | Silver-carrying aluminum silicate |
| Example 7 | Silver-carrying zirconium silicate |
| Example 8 | Silver-carrying silica gel |
| Example 9 | Silver-carrying titania |
| Example 10 | Silver-carrying calcium phosphate |
| Example 11 | $Ag_2O$ |
| Example 12 | $Ag_3PO_4$ |
| Comparative Example 1 | No addition of silver |

TABLE 2(1 - 1)

| | Width of the Inhibition Band (units:mm) | | |
|---|---|---|---|
| | Staphylococcus aureus | Bacillus subtilis | Escherichia coli |
| Example 1 | 1.3 | 1.6 | 1.7 |
| Example 2 | 1.1 | 1.0 | 1.2 |
| Example 3 | 1.5 | 1.9 | 1.3 |
| Example 4 | 0.8 | 0.3 | 0.5 |
| Example 5 | 1.7 | 1.8 | 1.4 |
| Example 6 | 2.0 | 2.1 | 2.4 |
| Example 7 | 2.4 | 2.0 | 2.7 |
| Example 8 | 1.5 | 1.1 | 1.2 |
| Example 9 | 2.1 | 2.5 | 2.6 |
| Example 10 | 2.8 | 2.4 | 3.0 |
| Example 11 | 2.2 | 1.8 | 2.8 |
| Example 12 | 3.0 | 2.2 | 3.2 |
| Comparative Ex. 1 | 0 | 0 | 0 |

TABLE 2(1 - 2)

| | Width of the Inhibition Band (units:mm) | | |
|---|---|---|---|
| | Salmonella | Klebsiella pneumoniae | Pseudomonas aeruginosa |
| Example 1 | 1.1 | 1.0 | 1.9 |
| Example 2 | 1.4 | 1.0 | 1.8 |
| Example 3 | 1.1 | 1.4 | 2.0 |
| Example 4 | 0.7 | 0.2 | 0.9 |
| Example 5 | 1.2 | 1.1 | 1.6 |
| Example 6 | 2.7 | 2.1 | 2.3 |
| Example 7 | 2.3 | 2.9 | 3.4 |
| Example 8 | 1.1 | 1.1 | 1.2 |
| Example 9 | 2.3 | 2.9 | 3.3 |
| Example 10 | 2.2 | 2.7 | 3.6 |
| Example 11 | 1.2 | 1.7 | 1.4 |
| Example 12 | 1.5 | 2.0 | 2.6 |
| Comparative Ex. 1. | 0 | 0 | 0 |

In the fungus resistance test, *Aspergillus niger, Penicillium funiculsssum, Cladosporium cladosporioides*, and *Aureobasidium pullulans* were employed as the sample fungal mycete. The fungal mycete incubation was conducted for 7 days and 14 days; no development of fungus was observed in any of the 12 bacterium in Examples 1~12. However, the development of fungus was confirmed in Comparative Example 1.

EXAMPLE 13

Initially, 100 g of silver phosphate was dispersed in 500 ml of water and agitated for 30 minutes at 25° C. Subsequently, 400 g of a fire resistant material, in which a composition of 55% kaolin, 37% feldspar and 8% quartz was previously blended, was added to the aforementioned, and the resultant mixture was agitated for 1 hour to produce an anti-bacterial and anti-fungal glaze composition for ceramic products with a solid content of 50%.

A conventional glaze was first applied to a tile substrate and dried at room temperature. The aforementioned slurry was then sprayed onto this resultant material at a proportion of 0.005 g/cm$^2$, dried at room temperature, and baked for 1 hour at a temperature of 1200° C. to produce an anti-bacterial/anti-fungal-treated test specimen. With regard to the color tone and surface shape of this test specimen, no differences were observed when compared to the test specimen obtained in Comparative Example 2.

Subsequently, the aforementioned test specimen was divided into 30×30 mm sections and sterilized. Under sterile conditions, *Escherichia coli, Pseudomonas aeruginosa, Staphylococcus aureus*, and an additional four types of slimy bacterium which were actually extracted from sanitary earthenware were respectively dispersed in phosphate buffer, cultivated in a bouillon, and diluted to a concentration on the order of $10^4$ CFU/ml. The test specimen was then inoculated with 0.1 ml of this diluted solution. After placing this specimen in an incubator for 24 hours at 37° C., the specimen was washed with a physiological saline solution and a portion therein was extracted. At same time, the *Escherichia coli* was used to inoculate a desoxycholate agar, while the other bacterium were used to inoculate normal agar culture media. After 48 hours for the *Staphylococcus aureus* and 18 hours for the other bacterium, the number of colonies formed in the petri dishes were counted. These results are shown in Table 3.

Comparative Example 2

The same test specimen was produced as in Example 13 with exception that the anti-bacterial and anti-fungal glaze composition for ceramic products was not employed. Similar tests were then conducted and these results are also shown in Table 3.

TABLE 3

| Bacterial Strain | Comparative concentration from Comparative Ex. 2 (CFU/ml) | Concentration following test from Example 13 (CFU/ml) | Sterilization rate (%) |
|---|---|---|---|
| *Escherichia coli* | $5.2 \times 10^4$ | <10 | >99.98 |
| *Pseudomonas aeruginosa* | $1.2 \times 10^4$ | <10 | >99.91 |
| *Staphylococcus aureus* | $3.7 \times 10^4$ | <10 | >99.97 |
| Extracted bacterium | $6.4 \times 10^4$ | <10 | >99.98 |

The calculation of the sterilization ratio was conducted by the following formula:

$$\text{Sterilization ratio (\%)} = \frac{A - B}{A} \times 100$$

A: Comparative concentration from Comparative Example 2

B: Concentration following test from Example 13

EXAMPLE 14

Silica sand and dehydrated borax were added to a commercially available borosilicate glass frit. Silver phosphate was further added to this mixture at a ratio of 1:9. After mixing well, the resultant mixture was then placed in a crucible and melted for 30 minutes at 1200° C. After directly placing the melt obtained into water, the resultant cooled and solidified material was coarse-crushed to produce the anti-bacterial and anti-fungal glaze composition for ceramic products of the present invention.

This aforementioned anti-bacterial and anti-fungal glaze composition for ceramic products possessed the following composition: 49% by weight of $SiO_2$, 8% by weight of $Al_2O_3$, 5% by weight of CaO, 10% by weight of $B_2O_3$, 5% by weight of $Na_2O$, 2% by weight of $K_2O$, 10% by weight of SrO, 8% by weight of Ag and 2% by weight of $P_2O_5$.

Subsequently, the aforementioned anti-bacterial and anti-fungal glaze composition for ceramic products was mixed with water in a 1:1 ratio, placed in a centrifugal ball mill and crushed to produce a sedimentating slurry.

This slurry was then sprayed onto tile to which a conventional zircon-type white glaze had previously been applied, and baked in an electric furnace for 30 minutes at 1200° C. The resultant material was then tested using *Escherichia coli* in the same manner as in the aforementioned Example 13. The results are shown in Table 4.

In addition, a halo test was also conducted using the aforementioned anti-bacterial and anti-fungal glaze composition for ceramic products which was cooled and solidified in a lump or powder state.

The halo test was performed by coating a normal agar culture medium with a liquid suspension of bacterium, placing either a 5×5×5 mm lump or 0.05 g of a powder of the aforementioned anti-bacterial and anti-fungal glaze composition for ceramic products onto this culture medium, and allowing this test specimen to sit in an incubator at 37° C. for 18 hours. Following this incubation, the width of the inhibition band formed at the periphery of the aforementioned anti-bacterial and anti-fungal glaze composition for ceramic products in a lump or powder state was measured. These results are shown in Table 5. In addition, values shown in Table 5 represent the widths (mm) of the inhibition bands.

The calculation of the sterilization ratio was conducted by the following formula:

$$\text{Sterilization ratio (\%)} = \frac{C - D}{C} \times 100$$

A: Comparative concentration from Comparative Example 3

B: Concentration following testing from Example 14 and Example 15

EXAMPLE 15

In the same manner as in Example 14, 5% by weight of the anti-bacterial and anti-fungal glaze composition for ceramic products manufactured in Example 13 was added to a conventional glaze, and this mixture was crushed and mixed in a centrifugal ball mill with an equal amount of water to produce a slurry.

This mixed slurry was then sprayed directly onto a tile substrate and baked under the same conditions as in Example 14. Fungus resistance and halo tests were then conducted on the resultant test specimen in the same manner as in Example 14. These results are shown in Table 4 and Table 5.

Comparative Example 3

A test specimen was manufactured and tested in the same manner as in Examples 14 and 15 with the exception that the anti-bacterial and anti-fungal glaze composition for ceramic products was not added. These results are also shown in Table 4 and Table 5.

TABLE 4

| | Example 14 | Example 15 | Comparative Example 3 |
|---|---|---|---|
| Concentration of bacterium following testing (CFU/ml) | $3.00 \times 10^3$ | $3.50 \times 10^3$ | $3.80 \times 10^6$ |
| Sterilization ratio | 99.92% | 99.91% | — |

TABLE 5

| | Width of the Inhibition Band (units:mm) | | |
| --- | --- | --- | --- |
| | Example 14 | Example 15 | Comparative Example 3 |
| Staphylococcus aureus | 2.27 | 1.86 | 0 |
| Pseudomonas aeruginosa | 3.94 | 3.44 | 0 |
| Escherichia coli | 4.20 | 3.62 | 0 |
| Trichophyton | 3.16 | 2.45 | 0 |

Field of Industrial Use

The anti-bacterial and anti-fungal glaze composition for ceramic products according to the present invention can be used to form an anti-bacterial and anti-fungal glaze layer and enamel surface with superior anti-bacterial and anti-fungal properties on the surfaces of ceramic products such as porcelain products, enamel products and the like. Consequently, the present invention can be effectively used on the surfaces of materials which require superior anti-bacterial and anti-fungal properties such as commodes, bath tubs, wash basins, water tanks, water supply vessels, hand rails, tile, dental sanitary material and the like.

In particular, since the anti-bacterial and anti-fungal glaze composition for ceramic products possesses a superior heat resistance, there is no sinking of the silver component into the interior or bottom portions of the glaze, and hence anti-bacterial and anti-fungal properties can be effectively exhibited on the surfaces of ceramic products.

In this manner, the present invention is ideal for use in wash basins, tile, commodes, bath tubs and the like employed in places utilized by an unspecified large amount of persons such as hospitals, hotels, public facilities and other places which, in particular, require anti-bacterial and anti-fungal properties.

What is claimed is:

1. An anti-bacterial and anti-fungal ceramic product having an anti-bacterial and anti-fungal glaze layer comprising at lease one silver-containing substance selected from the group consisting of halogenated silver, silver salts of inorganic acids, silver salts of organic acids, silver oxide, silver hydroxide, and an ion-exchange compound carrying silver via an ion-exchange reaction;

and a material selected from the group consisting of refractory compositions, glass compositions, and combinations thereof.

2. An anti-bacterial and anti-fungal ceramic product according to claim 1, wherein said ion-exchange compound carrying silver via an ion-exchange reaction is at least one compound selected from the group consisting of aluminum silicate compounds, phosphate compounds, titania compounds, and silica compounds.

3. An anti-bacterial and anti-fungal ceramic product according to claim 1, wherein said refractory material is at least one member selected from the group consisting of clay, agalmatolite, diaspore, bauxite, and alumina silicate.

4. An anti-bacterial and anti-fungal ceramic product according to claim 3, wherein said sanitary earthenware is a commode.

5. An anti-bacterial and anti-fungal ceramic product according to claim 3, wherein said sanitary earthenware is a wash bowl.

6. An anti-bacterial and anti-fungal ceramic product according to claim 3, wherein said sanitary earthenware is a bath tub.

7. An anti-bacterial and anti-fungal ceramic product according to claim 3, wherein said sanitary earthenware is a wash basin.

8. An anti-bacterial and anti-fungal ceramic product according to claim 1, wherein said glass composition is at least one oxide glass selected from the group consisting of soda-lime glass, lead glass, borosilicate glass, and aluminosilicate glass.

9. An anti-bacterial and anti-fungal ceramic product according to claim 1, wherein said ceramic product is a porcelain product.

10. An anti-bacterial and anti-fungal ceramic product according to claim 1, wherein said ceramic product is an enamel product.

11. An anti-bacterial and anti-fungal ceramic product according to claim 10, wherein said enamel product is an enamel bath tub.

12. An anti-bacterial and anti-fungal ceramic product according to claim 10, wherein said enamel product is an enamel plate.

13. An anti-bacterial and anti-fungal ceramic product according to claim 1, wherein said ceramic product is sanitary earthenware.

14. An anti-bacterial and anti-fungal ceramic product according to claim 1, wherein said ceramic product is a tile.

15. An anti-bacterial and anti-fungal ceramic product according to claim 1, wherein said ceramic product is tableware.

* * * * *